US005954637A

United States Patent [19]
Francis

[11] Patent Number: 5,954,637
[45] Date of Patent: *Sep. 21, 1999

[54] LAPAROSCOPE

[75] Inventor: William J. Francis, Quincy, Mass.

[73] Assignee: United States Surgical Corporation, Norwalk, Conn.

[ * ] Notice: This patent is subject to a terminal disclaimer.

[21] Appl. No.: 08/843,825

[22] Filed: Apr. 21, 1997

Related U.S. Application Data

[63] Continuation of application No. 08/546,248, Oct. 20, 1995, Pat. No. 5,634,881.

[51] Int. Cl.[6] .................................................. A61B 1/002
[52] U.S. Cl. ........................ 600/138; 600/133; 600/920
[58] Field of Search .................................. 600/920, 131, 600/133, 136, 162, 172, 174, 121, 128, 138

[56] References Cited

U.S. PATENT DOCUMENTS

| | | |
|---|---|---|
| 4,148,550 | 4/1979 | MacAnally . |
| 4,148,551 | 4/1979 | MacAnally . |
| 4,440,157 | 4/1984 | Shishido . |
| 4,576,147 | 3/1986 | Hashiguchi . |
| 4,624,243 | 11/1986 | Lowery et al. . |
| 4,742,818 | 5/1988 | Hughes et al. . |
| 4,745,470 | 5/1988 | Yabe et al. . |
| 4,779,613 | 10/1988 | Hashiguchi et al. . |
| 4,790,295 | 12/1988 | Tashiro ..................................... 600/920 |
| 4,854,302 | 8/1989 | Allred, III . |
| 4,882,154 | 11/1989 | Oxford et al. ........................... 600/920 |
| 4,919,112 | 4/1990 | Siegmund . |
| 4,964,710 | 10/1990 | Leiner . |
| 5,125,394 | 6/1992 | Chatenever et al. ..................... 600/162 |
| 5,190,028 | 3/1993 | Lafferty et al. . |
| 5,299,560 | 4/1994 | Hatori . |
| 5,335,647 | 8/1994 | Brustad ................................... 600/920 |
| 5,352,237 | 10/1994 | Rodak et al. . |
| 5,359,453 | 10/1994 | Ning . |
| 5,369,525 | 11/1994 | Bala et al. . |
| 5,412,504 | 5/1995 | Leiner et al. . |
| 5,416,634 | 5/1995 | Ning . |
| 5,447,148 | 9/1995 | Oneda et al. . |
| 5,447,343 | 9/1995 | Gajewski et al. ........................ 600/133 |
| 5,456,245 | 10/1995 | Bornhop et al. ........................ 600/920 |
| 5,458,133 | 10/1995 | Yabe et al. . |
| 5,538,496 | 7/1996 | Yabe et al. . |
| 5,554,100 | 9/1996 | Leiner et al. ............................ 600/920 |

*Primary Examiner*—Richard J. Apley
*Assistant Examiner*—Ira Hatton

[57] ABSTRACT

A multi-use disposable endoscope capable of being sterilized and reused for a number of surgical procedures and then discarded is disclosed. The endoscope is adapted to withstand a number of sterilization cycles without experiencing degradation of the functional systems of the scope, and yet retains the cost effective qualities of a disposable endoscope. The endoscope preferably is formed in accordance with methods utilized for manufacturing a disposable endoscope, e.g., incorporating inexpensive plastic components for the housing sections of the scope as well as for the various systems of the scope. Particular attention is directed to adequately sealing potential leakage areas of the endoscope, such as the distal end of the endoscope and the juncture of the endoscopic portion and the eyepiece section.

6 Claims, 5 Drawing Sheets

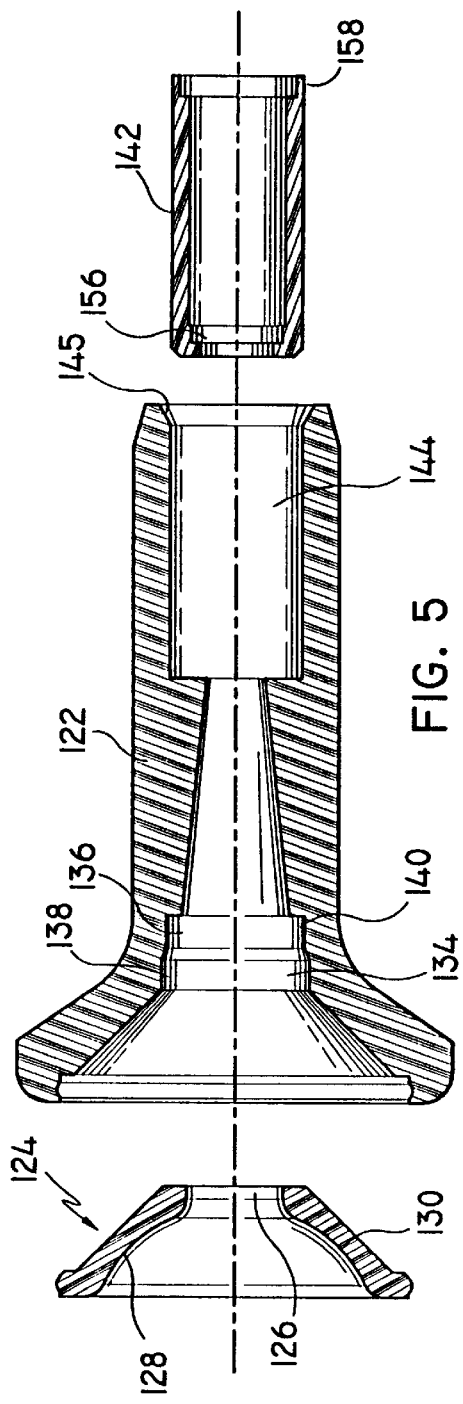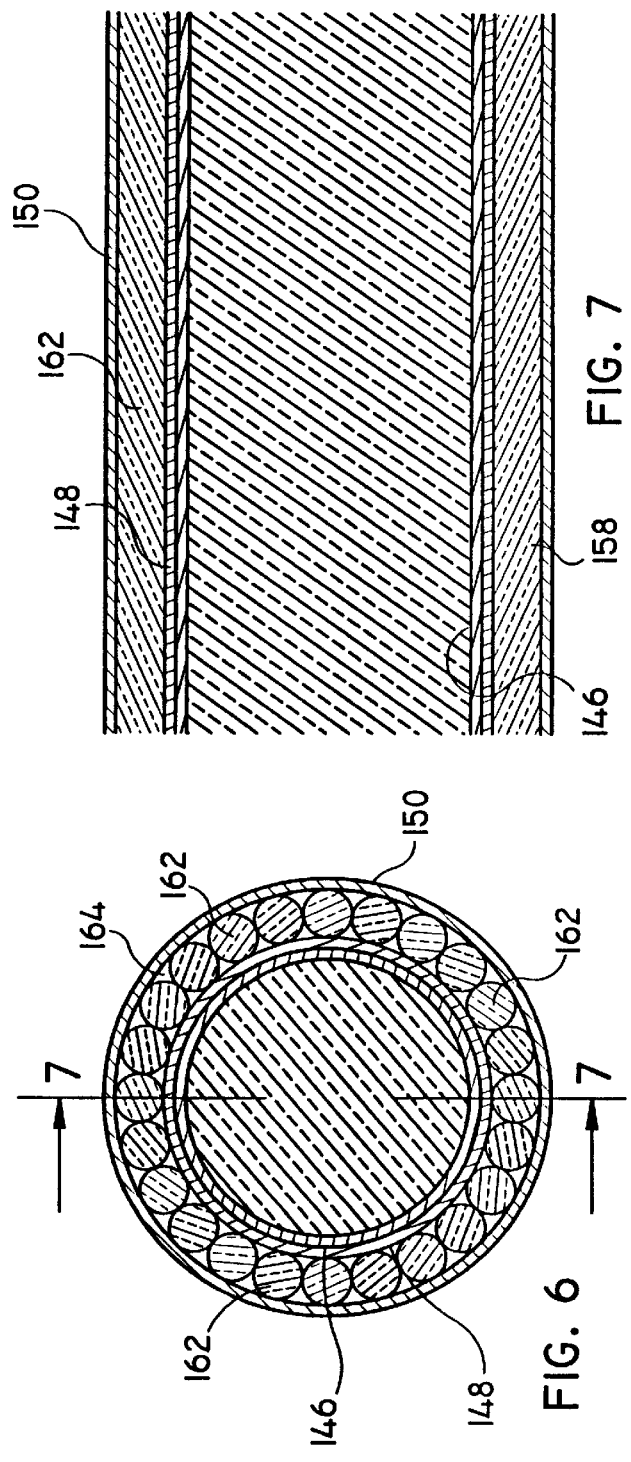

LAPAROSCOPE

This is a continuation, of U.S. application Ser. No. 08/546,248, filed Oct. 20, 1995, now U.S. Pat. No. 5,634,881.

BACKGROUND

1. Field of the Disclosure

The present disclosure generally relates to endoscopes for use in endoscopic surgery and, in particular, to a low cost multi-use disposable laparoscope.

2. Background of the Related Art

Endoscopes have long been used in surgery to view internal portions of a patient's body through a narrow incision in the body exterior or through a naturally occurring hollow viscus. Endoscopes are long, slender instruments having a shaft which is either rigid or flexible, depending upon the procedure being performed. In general, endoscopes include an objective lens positioned adjacent a distal end and an image transmission system which may include a fiber optic bundle, relay rods or lenses, or a solid state sensor to transmit the image to the viewer. Endoscopes also are usually equipped with an illumination system, such as a fiber optic bundle, which illuminates the area being imaged. A camera adapter may be provided at the proximal end of the endoscope to permit the image to be displayed on a monitor for viewing by the entire surgical team.

Traditionally, endoscopes have been manufactured as reusable instruments. A reusable endoscope is intended to be used for a number of surgical procedures and requires cleaning and sterilization after each procedure. Reusable endoscopes are generally expensive to manufacture due in part to the expense of the components of the various systems, such as glass optics, which are required to function at high levels of performance after repeated re-sterilization for prolonged periods of time.

Also adding to the expense of reusable endoscopes are the materials and provisions required to appropriately seal the endoscope to prevent leakage of body fluids within the scope during the surgical procedure and, more particularly, to prevent leakage of sterilization fluids within the scope during repeated sterilization procedures. During a sterilization procedure, the endoscope may be subjected to steam temperatures in excess of 130° C. for periods lasting as long as 1–2 hours. The steam environment has a substantial degrading affect on the seal areas of the endoscope. Moreover, the chemicals utilized during sterilization are also quite invasive to the scope, thus presenting additional concerns. Because multiple sterilizations and other handling eventually result in degradation in optical performance, reusable endoscopes frequently are returned to the manufacturer to be refurbished at substantial additional expense.

Recently, efforts have been focused on the manufacture of disposable endoscopes, i.e., endoscopes contemplated for disposal after a single use. An example of a disposable endoscope is the SURGIVIEW™ laparoscope manufactured by U.S. Surgical Corporation of Norwalk, Conn. Disposable endoscopes generally are manufactured cost-effectively, typically utilizing less expensive plastic components or parts, as appropriate, in lieu of steel and glass, for the housing and the various systems of the scope including the optical and illumination systems. In addition, since disposable endoscopes are not subjected to subsequent sterilization procedures for cleaning, disposable scopes need not be sealed as effectively as reusable scopes, thereby further reducing the cost of disposable scopes. Accordingly, disposable endoscopes are not adapted to favorably undergo repeated sterilization procedures, and, if exposed to multiple sterilizations, experience leakage of steam and chemicals into the scope and rapid degradation of endoscope performance.

Notwithstanding the relatively low cost of disposable endoscopes, there is a perception in the surgical community that reusable endoscopes are more economical, notwithstanding high initial investment costs, cleaning and sterilization costs, and expensive repair costs. In view of the relative expense involved in the purchase and maintenance of reusable endoscopes, it would be desirable to provide a disposable endoscope having a lower per-use cost than a reusable endoscope.

SUMMARY OF THE DISCLOSURE

Accordingly, the present disclosure is directed to a low cost multi-use disposable endoscope adapted to withstand repeated sterilizations without experiencing leakage and consequent degradation of the functional systems of the scope until the scope has been used a sufficient number of times to render the per-use cost of the scope cost effective when compared to the per-use cost of a reusable endoscope. The multi-use disposable endoscope retains the cost effective qualities of a disposable endoscope so that it may be discarded after optical performance degrades to an unacceptable level. Preferably the multi-use disposable endoscope is made substantially in accordance with methods utilized for manufacturing a disposable endoscope, e.g., incorporating inexpensive plastic components for the housing sections of the scope as well as for the various optical systems of the scope. In addition, however, particular attention is directed to adequately sealing potential leakage areas of the endoscope, such as the distal face of the scope, the juncture of the endoscopic portion and the frame, the eyepiece section, etc., sufficiently to resist leakage of sterilization fluids and chemicals during numerous sterilizations.

In one preferred embodiment, the low cost reusable endoscope includes a frame dimensioned to be engaged by the hands of a surgeon and an elongated portion connected to the frame and extending distally therefrom. The elongated portion includes an outer tube defining a longitudinal axis, an inner tube coaxially disposed within the outer tube and a lens tube coaxially disposed within the inner tube. An illumination system consisting of a plurality of optical fibers is disposed within a generally annular space defined between the outer and inner tubes. An optical system including at least a relay lens arrangement is disposed within the lens tube. The low cost reusable endoscope further includes an eyepiece which is mounted to the frame. The eyepiece includes at least one eyepiece lens in alignment with the optical axis to permit viewing of the image transferred by the relay lens arrangement.

The frame or housing of the endoscope preferably includes two half sections. One half section includes a groove extending along its periphery. The other half section includes a correspondingly dimensioned and configured tongue extending along its periphery. The peripheral groove and tongue arrangement of the half sections interfit to form a fluid tight seal at this juncture, thereby substantially preventing fluids from entering the frame and penetrating the optical and illumination systems of the scope. In one preferred embodiment, a cement sealant is applied to the peripheral groove prior to assembly of the half sections, which, upon curing, provides a cement seal about the entire periphery of the frame. This cement seal, in conjunction with the fluid tight seal effectuated by the tongue and groove arrangement, ensures that the frame is impervious to sterilization fluids for a number of sterilization procedures. As a result, the endoscope may repeatedly be used and re-sterilized after each use.

The endoscope may further include an eyepiece sleeve. The eyepiece sleeve is coaxially mounted about a proximal end of the lens tube and is accommodated within a correspondingly dimensioned longitudinal recess defined in the eyepiece. The eyepiece sleeve has a recessed area which defines a gap or annular recess between the inner surface of the eyepiece sleeve and the outer surface of the lens tube. This gap receives a sealant which subsequently cures to form a fluid tight seal about the lens tube. Thus, any moisture or other contaminants which may be present in the frame or housing are prevented from penetrating the optical system within the lens tube and degrading the functional characteristics of the optical system. The eyepiece sleeve also functions in supporting the lens tube to ensure a coaxial relation of the lens tube and the outer tube. The eyepiece also may have an annular recess surrounding the eyepiece sleeve filled with sealant, and the recesses filled with sealant may be protected by a further epoxy layer.

A method for forming a low cost reusable disposable endoscope also is disclosed.

BRIEF DESCRIPTION OF THE DRAWINGS

Preferred embodiment(s) of the present disclosure are of described herein with reference to the drawings wherein:

FIG. 2A is a cross-sectional view of a portion of the housing taken along lines 2A—2A of FIG. 2, illustrating the tongue and groove arrangement for securing the half sections of the housing portion together in fluid tight relation;

FIG. 5 is a cross-sectional view of the eyepiece unit, with parts separated, including the eyepiece cup, the eyepiece and the eyepiece sleeve;

FIG. 6 is a cross-sectional view taken along the lines 6—6 of FIG. 4 illustrating the annular arrangement of the fiber optic array disposed within an annular space defined between the outer fiber tube and the inner fiber tube; and FIG. 7 is a cross-sectional view taken along the lines 7—7 of FIG. 6.

DETAILED DESCRIPTION OF THE PREFERRED EMBODIMENT(S)

Figure 1:
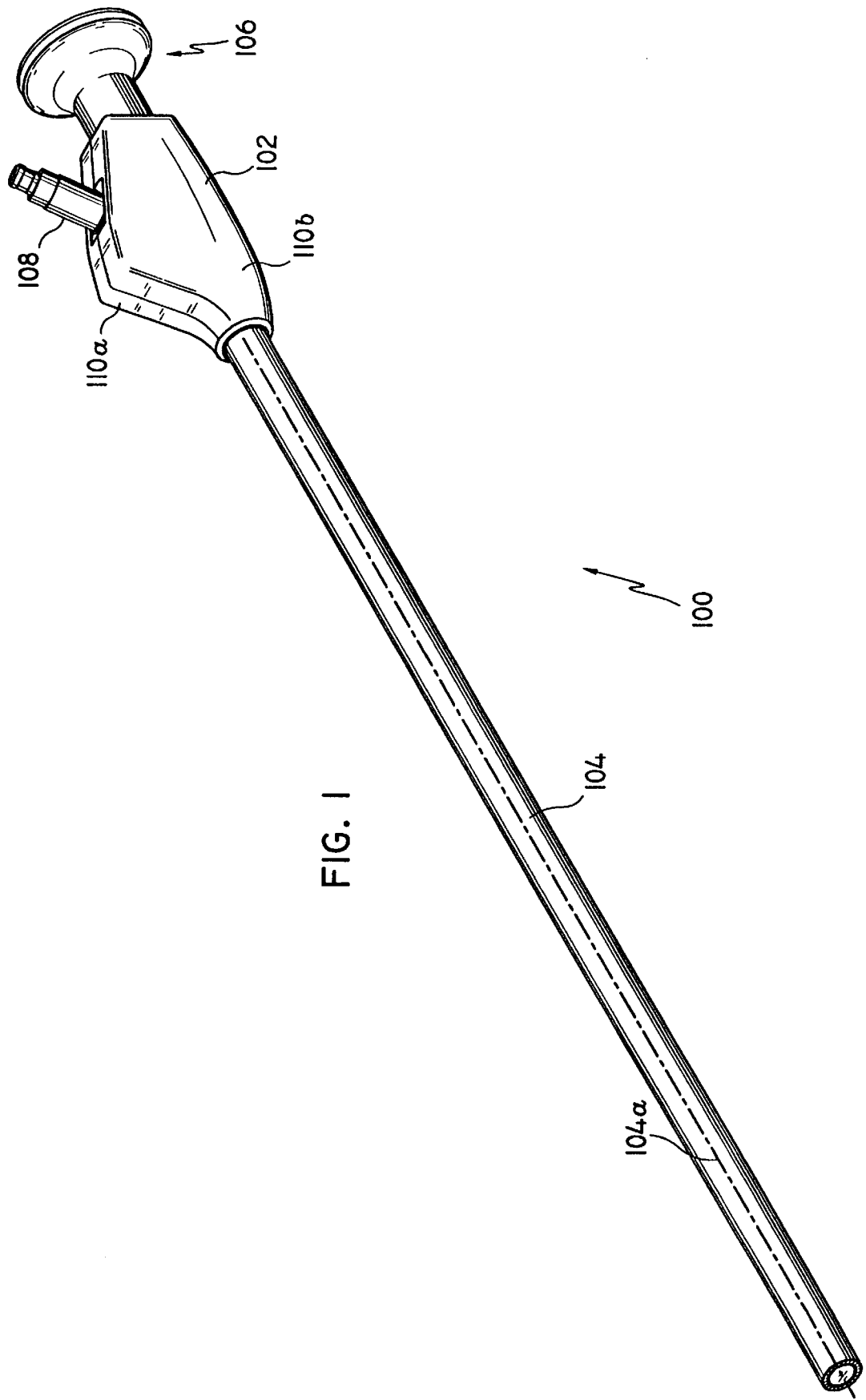
FIG. 1 is a perspective view of the endoscope in accordance with the principles of the present disclosure.

Referring now to the drawings, in which like reference numerals identify similar or identical elements throughout the several views, FIG. 1 illustrates, in perspective view, a multi-use disposable endoscope in accordance with the principles of the present disclosure. Endoscope 100 is preferably a laparoscope, i.e., a scope contemplated for use in laparoscopic surgical procedures. Laparoscopic surgery is surgery conducted within the peritoneal cavity of the patient, and involves insufflation of the peritoneal cavity with appropriate insufflation gases to raise the cavity wall, thereby permitting enhanced access to the internal organs within the cavity.

Laparoscope 100 is intended to be reused for a limited number of surgical procedures, e.g., up to about 50 surgical procedures, and is advantageously designed and configured to withstand the adverse conditions of a sterilization procedure after each use while maintaining its imperviousness to sterilization fluids, body fluids, etc., for a sufficient number of re-sterilizations to render the laparoscope very cost effective. In referring to a number of re-sterilizations, it is contemplated the endoscope may be re-sterilized fifteen to twenty times using ethylene oxide sterilization cycle or Steris™ technique. Laparoscope 100 can be manufactured cost effectively preferably at a comparable cost to that of a disposable endoscope.

Figure 2:
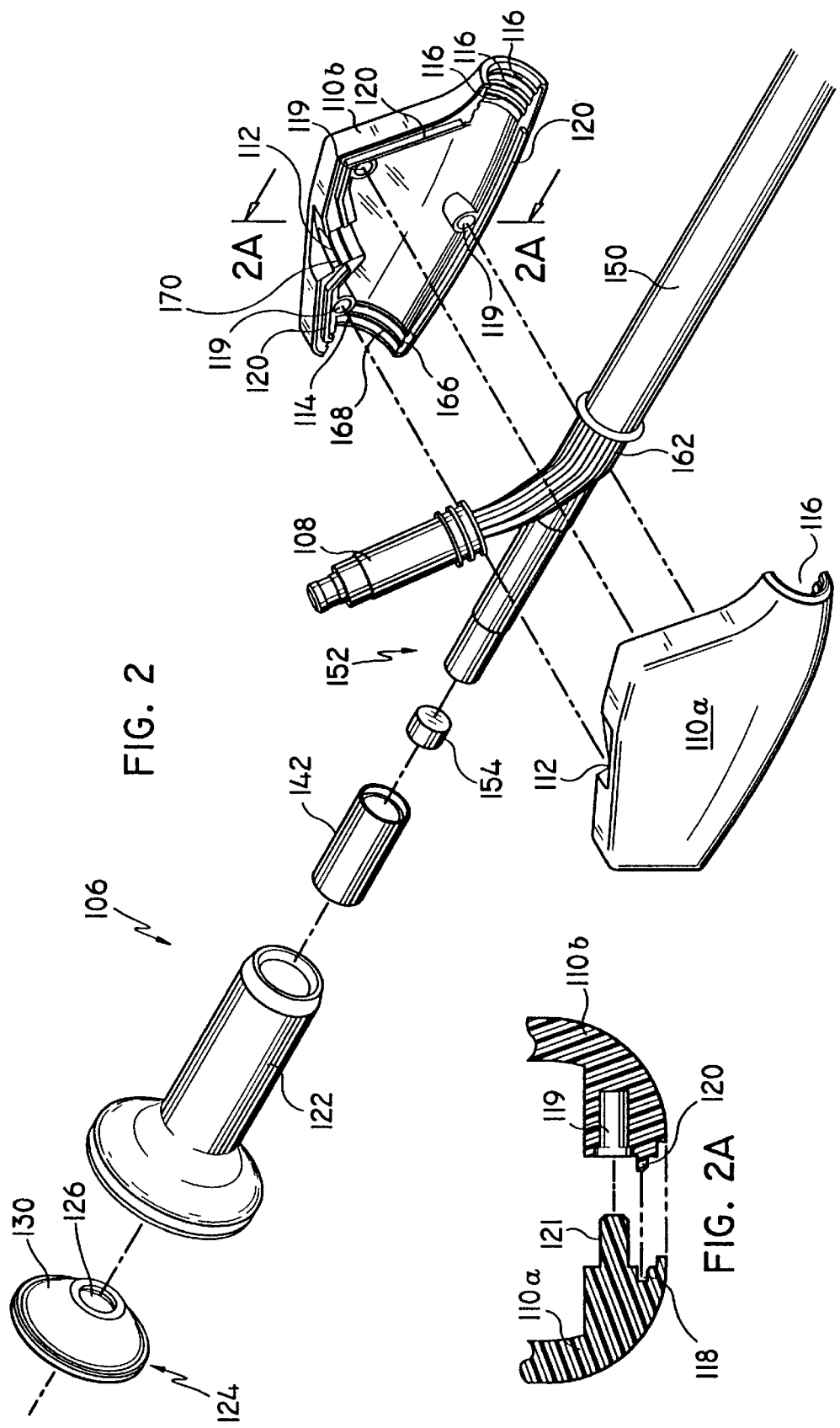
FIG. 2 is a perspective view with parts separated of the housing portion of the endoscope of FIG. 1.

Referring now to FIGS. 1–2, laparoscope 100 includes housing 102 and endoscopic portion 104 extending from the housing 102. Housing 102 supports an eyepiece unit, generally identified as reference numeral 106, which contains the eyelens assembly for viewing an image of an object formed by the optical system. Housing 102 also supports an illuminator connector 108. Illuminator connector 108 connects a conventional light guide (not shown) which supplies illuminating light to the illumination system of the laparoscope.

Housing 102 consists of two half sections 110a, 110b, connected to each other along their peripheries. Half sections 110a, 110b are preferably fabricated from a suitable inexpensive plastic material such as polycarbonate, nylon or glass filled nylon. Referring to FIG. 2, each half section 110a, 110b includes a correspondingly dimensioned arcuate or semicircular recess 112, which, in the assembled condition of the housing 102, defines an illuminator port for accommodating illuminating connector 108. Similarly, each half section 110a, 110b includes a semi-circular opening or recess 114 at its proximal end and a semi-circular opening or recess 116 at its distal end to accommodate the eyepiece unit 106 and the endoscopic portion 104, respectively.

Referring now to FIG. 2, in conjunction with FIG. 2A, housing half sections 110a, 110b further include a tongue and groove arrangement for fixedly securing the half sections together. In particular, housing half section 110a has a groove 118 extending about its periphery. Housing half section 110b has a correspondingly dimensioned and configured peripheral tongue or rib 120 which is received within groove 118. Groove 118 and tongue or rib 120 are advantageously dimensioned to form a fluid-tight fit between the two components upon assembly of the housing 102. In particular, the tongue and groove arrangement forms a fluid tight seal at the interface of half sections 110a, 110b, thus, precluding the passage of fluids within housing 102 during and subsequent to sterilization. In addition, the housing halves include a plurality of pins 121 dimensioned for snap lock engagement into recesses 119 to secure the housing halves together. Additional adhesives or sealants may be disposed between ribs 120 and grooves 118, and/or pins 121 and recesses 119.

Figure 4:
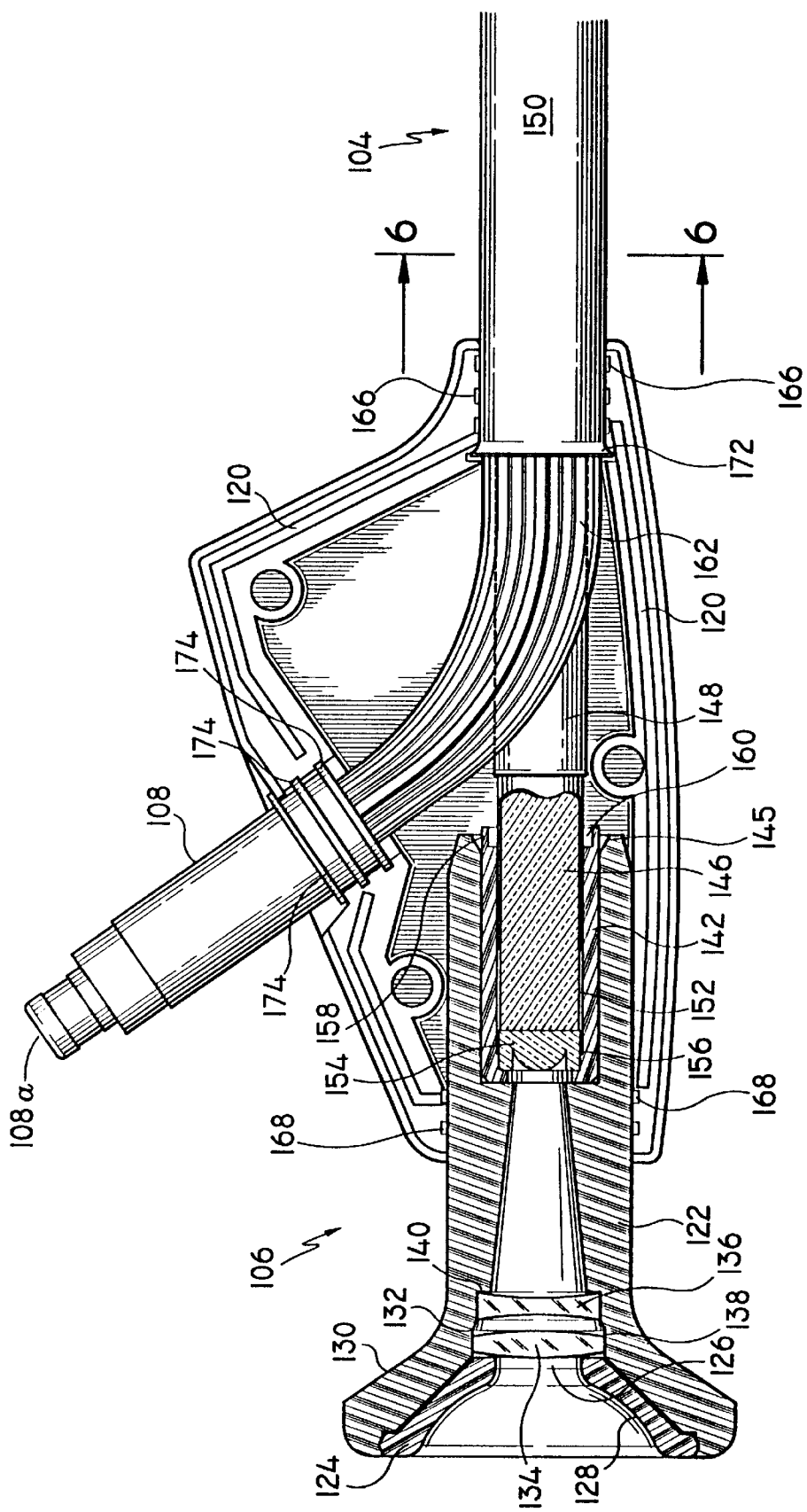
FIG. 4 is a cross-sectional view of the the housing portion of the endoscope illustrating the interrelationship of housing with the eyepiece unit, the optical lens optical tube, and the endoscopic portion.

Referring now to FIGS. 2, 4 and 5, eyepiece unit 106 includes eyepiece 122 and eyepiece cup 124 affixed to the proximal end face of the eyepiece 122. Eyepiece cup 124 includes a central aperture 126 to permit viewing of the image transferred by the optical system of the laparoscope. Inner surface 128 defines a smooth generally continuous arcuate surface, which advantageously prevents the accumulation of sterilization fluids within this area during and subsequent to sterilization procedures. In particular, by virtue of the continuous arcuate shape of inner surface 128, no "land areas" are formed where sterilization fluids may accumulate. Any accumulation of sterilization fluids in this area would eventually degrade the integrity of the seal formed at the proximal end of the eyepiece unit 106. Eyepiece cup 124 is adhered to eyepiece 122 with a suitable adhesive.

An eyelens arrangement 132 is mounted within eyepiece 122 (FIG. 4). The eyelens arrangement 132 provides a magnified image of the object transferred by the optical system and possesses two lenses 134, 136 mounted within correspondingly dimensioned recesses 138, 140 formed within eyepiece 122. The eyelens arrangement 132 may be any conventional eyelens assembly preferably fabricated from suitable inexpensive polymeric materials. The proximal end surface of lens 134 directly abuts eyepiece cup 124 as shown which conveniently exposes the lens surface to facilitate cleaning. Lenses 134, 136 are sealed and adhered to one another and to the housing to seal the end of eyepiece unit 106 using a suitable sealant such as Norland 68, (Norland Products, Inc., North Brunswick, N.J.). Inner eyepiece cup 124 is similarly adhesively sealed to eyepiece 122. Eyepiece unit 106 further includes an eyepiece sleeve 142 which is received within a correspondingly dimensioned cylindrical opening 144 at the distal end of eyepiece 122. The distal end of eyepiece 122 includes a tapered portion which defines a gap 145 between the eyepiece 122 and eyepiece sleeve 142. The significance of eyepiece sleeve 142 will become apparent from the description provided hereinbelow.

Figure 3:
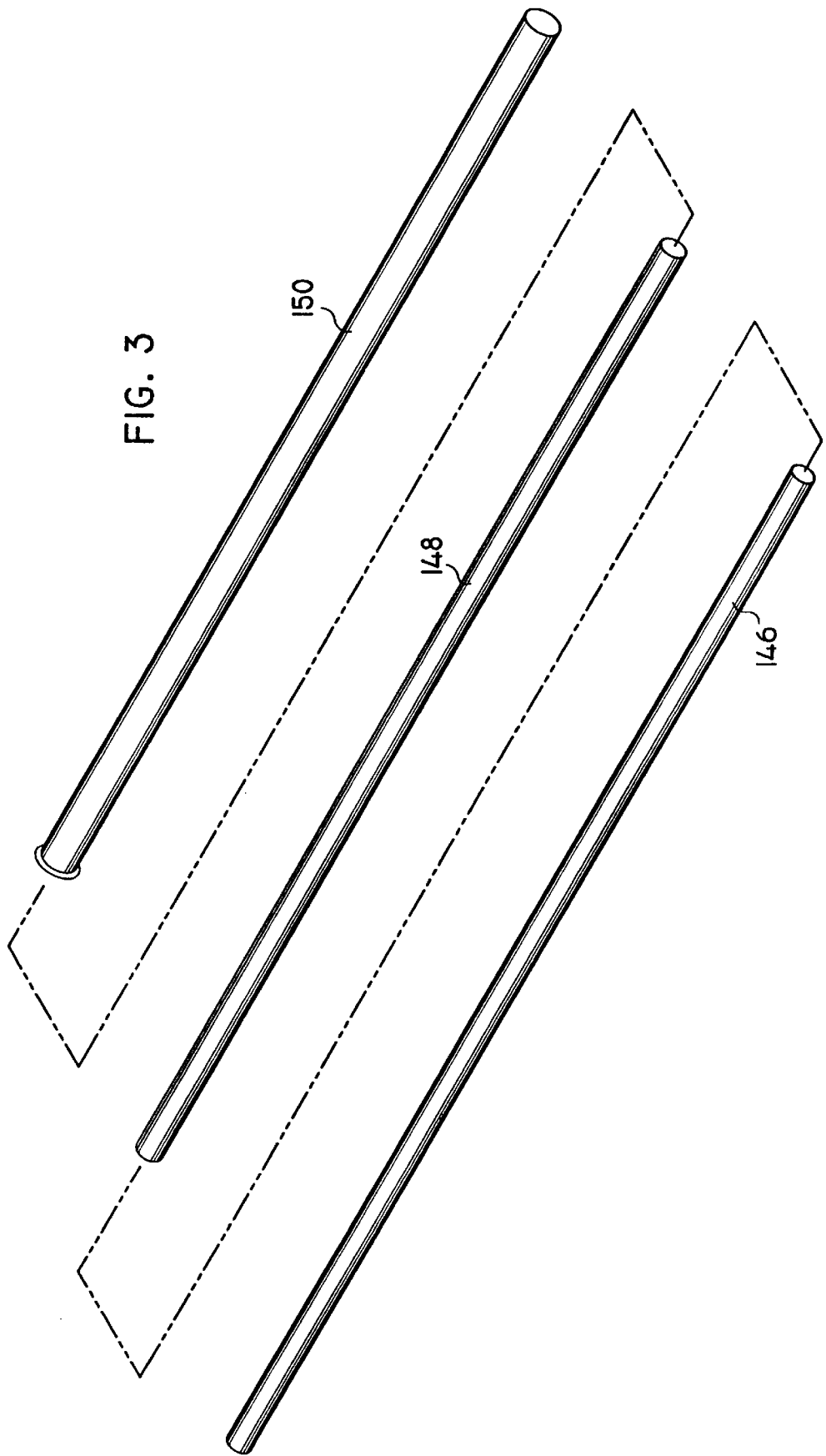
FIG. 3 is a perspective view with parts separated of the endoscopic portion of the endoscope of FIG. 1 illustrating the outer fiber tube, inner fiber tube and the central optical lens tube.

Referring now to FIGS. 1, 3 and 4, endoscopic portion 104 of laparoscope 100 defines longitudinal axis 104a and consists of central optical lens tube 146 and inner and outer fiber tubes 148, 150, respectively. Optical lens tube 146 houses the optical components constituting the objective and relay lens arrangements of the optical system of laparoscope 100. Generally, the objective lens arrangement forms an image of the object being viewed and the relay lens arrangement transfers the image through the endoscopic portion. As discussed above, the eye lens arrangement permits viewing of the image.

One optical system suitable to be mounted within optical lens tube 146 for use in laparoscope 100 is disclosed in U.S. Pat. No. 4,964,710 to Leiner, the contents of which are incorporated herein by reference. The optical system in the '710 patent discloses a relay lens arrangement including a plurality of axially aligned polymeric curved spaced apart lenses and a plurality of axially aligned plano glass cylinders positioned intermediate the spaced lenses. The optical components of the '710 patent optical system are relatively inexpensive and are contemplated for use in a disposable endoscope. Further details of optical systems constructed in accordance with the foregoing system are set forth in U.S. Pat. No. 5,412,504, the contents of which are incorporated herein by reference. Other optical systems may be suitable as well. For example, the optical systems disclosed in U.S. Pat. Nos. 5,359,453 and 5,416,634 may be suitable as well.

As best depicted in FIG. 4, the proximal end of optical lens tube 146 extends beyond inner and outer fiber tubes 148, 150 in the assembled condition of laparoscope 100 where it is accommodated within eyepiece sleeve 142 disposed within eyepiece 122. Eyepiece sleeve 142 stabilizes and maintains the concentric arrangement of optical lens tube 146 about the longitudinal axis 104a of endoscopic portion 104 thereby ensuring that the optical viewing axis of the optical system coincides with longitudinal axis 104a of the endoscopic portion 104. In a preferred arrangement, the first lens component, identified generally by reference numeral 152, of the relay lens system extends beyond the proximal end of optical lens tube 146 with the proximal most lens 154 of the component 152 abutting an inner surface 156 of the sleeve 142. Lens tube 146 extends at least partially into the bore of eyepiece sleeve 142. The outer diameter of optical lens tube 146 preferably approximates the inner diameter of inner lens tube 148 to form a friction fit between the two components. As depicted in FIGS. 4 and 5, eyepiece sleeve 142 also includes a distal recessed portion 158 defining a bore portion with a cross-sectional dimension or diameter greater than the cross-sectional dimension or diameter of lens tube 146 and greater than the remaining diameter or bore of the eyepiece sleeve. Recessed portion 158 defines a gap 160 between the inner surface of sleeve 142 and the outer surface of lens tube 146 in the assembled condition of the apparatus. Gap 160 receives a sealant during assembly of endoscope 100 as will be discussed.

Referring now to FIGS. 4, 6 and 7, the illumination system of laparoscope 100 includes a plurality of optical fibers 162 extending within an annular space 164 defined between inner and outer lens fiber tubes 148, 150 thereby forming an annular array of the fibers 162 as best depicted in FIG. 6. The fibers 162 extend at their proximal ends within illuminating coupler 108. Optical fibers 162 may be fabricated from glass or, more preferably, inexpensive polymeric materials, and define a diameter substantially equal to the distance between the inner and outer fiber tubes 148, 150. The distal end of endoscope portion 104 preferably is sealed with an adhesive such as Norland 68.

Assembly of the Laparoscope

Assembly of the laparoscope will now be described. The optical system is assembled with the individual illumination fibers 162 within the annular space 164 (FIG. 6) defined between inner and outer fiber tubes 148, 150 and the ends of fibers 162 cut, ground and polished. Optical lens tube 146 containing the objective and relay lens arrangements is disposed within inner fiber tube 148. The distal end faces of the respective tubes 146, 148 are flush. As noted above, and best depicted in FIG. 4, in this assembled position, the proximal end of optical lens tube 146 extends beyond the proximal end of inner fiber tube 148 as provided through the difference in lengths between the two components. Inner fiber tube 148 and optical lens tube 146 may be secured, if desired, to each other by conventional means such as with the use of adhesives or the like.

The proximal end portions of fibers 162 (i.e., the fiber portions extending beyond the proximal end of outer fiber tube 150) (FIG. 4) may be cemented together if desired.

A sealant is applied to the distal end face of the scope to completely seal the distal end face, i.e., the end surfaces of the inner and optical fiber tubes 148, 150 and outer lens tube 146 as well as the end faces of the optical fibers 162. A suitable sealant for this purpose is Norland 68. Once the sealant is cured, it is ground and polished so as to enhance its light conveying properties. This preferred sealing method ensures that a fluid-tight seal is provided at the distal end face.

Thereafter, illuminator coupler 108 is positioned onto the proximal end portions of optical fibers 162 and maneuvered whereby the proximal end faces or surfaces of the fibers 162 are flush with the entry end 108a (FIG. 4) of the illuminator coupler. Illuminator coupler 108 is adhered to optical fibers 162 and the sealant is applied to entry end 108a and the proximal end faces of the fibers 162 to prevent leakage of fluids therein. Upon curing, the seal is ground and polished in the manner described above.

Assembly is continued by mounting eyepiece cup 124 to eyepiece 122. It is to be noted that lenses 134, 136 may already be mounted within recesses 138, 140 of the eyepiece. Eyepiece cup 124 is preferably secured to eyepiece 122 with the use of suitable adhesives, cements, etc. In the mounted condition, the distal end surface of eyepiece cup 124 abuts directly against lens 134 of the eyelens arrangement. Lenses 134, 136 are adhesively secured in place and a seal is formed between lens 134, eyepiece cup 124 and eyepiece 122 using a suitable sealant, such as Norland 68.

Eyepiece sleeve 142 is then positioned over the proximal end of optical lens tube 146. As noted above, in the preferred embodiment, the first lens component 152 of the relay lens system extends proximally from optical lens tube 146. With this arrangement, the outer lens 154 of the lens component 152 is positioned to abut against inner shelf 156 of eyepiece sleeve 142 with the proximal end of optical lens tube 146 terminating at approximately the midpoint of the sleeve 142. Eyepiece sleeve 142 may be adhered to optical lens tube 146, if desired, using a suitable adhesive such as medical grade cyanoacrylate (LOCTITE CORP.).

With further reference to FIGS. 4 and 5, a sealant is applied within the gap 160 defined between the recessed portion 158 and lens tube 146. The sealant cures to form a fluid tight seal at the interface of the distal end of the eyepiece sleeve 142 and the outer surface of optical lens tube 146. This seal further ensures that any moisture or other contaminants within housing 102 will not penetrate the optical system and adversely affect the functioning of this system. Norland 68 is preferred. A sealant such as Norland 68, is then applied to gap 145 defined between eyepiece 122 and eyepiece sleeve 142 to further enhance the sealing characteristics. As an added measure of protection, a further layer may be applied over the Norland 68 to protect the Norland 68 sealant from degradation due to exposure to sterilizing agents. Thus, it is contemplated that an epoxy layer, such as CONAP epoxy (Combined Supply & Equipment Co., Inc., Buffalo, N.Y.), may be applied over the Norland 68 to further seal the juncture of optical lens tube 146, sleeve 142 and eyepiece 122.

Referring now to FIGS. 2 and 4, assembly of half sections 110a, 110b to the remaining components will be discussed. Prior to assembly, an appropriate cement may be applied within peripheral groove 118 of half section 110a (FIG. 2A), such as CONAP epoxy adhesive. In a preferred method, cement is applied to both housing halves within parallel grooves 166 adjacent opening 116, parallel grooves 168 adjacent opening 114 and parallel grooves 170 adjacent recesses 112. Thereafter, half sections 110a, 110b are secured to each other by the interengagement of the tongue and groove arrangement of the half sections 110a, 110b and by pins 121 in recesses 119. In the assembled condition, flange 172 (FIG. 4) of outer fiber tube 150 is accommodated within the first groove of parallel grooves 166 and flanges 174 of illumination coupler 108 are accommodated within grooves 170. Thus, by application of the cement about the periphery of half section 110a, a further cement seal is formed about the entire peripheral area. In particular, with reference to FIG. 4, a fluid tight seal is formed at the junctures of the endoscopic portion 104 and housing 102, eyepiece 106 and the housing 102 and illuminator coupler 108 and the housing 102. This fluid tight cement seal, in conjunction with the fluid-tight snap lock fit created by the tongue and groove arrangement and pins and recesses, ensures that the entire housing 102 is substantially impervious to fluids, including sterilization fluids, body fluids, etc. Alternatively, or perhaps in addition to the tongue and groove arrangement and cement, it may be desirable to fill the entire interior of housing 102 with epoxy for further assurance that the seal is not compromised.

It has been found that an endoscope constructed in accordance with this description advantageously may be re-sterilized many times for repeated use. Indeed, it has been found that the endoscope functions well even after experiencing as many as fifteen to twenty ethylene oxide sterilization cycles with at least two cold sterilizations in a 2% gluteraldehyde solution between each such ethylene oxide sterilizations, i.e., in excess of fifty uses under common hospital practices. Nevertheless, the endoscope is relatively inexpensive to manufacture, and economically may be disposed of when, after numerous sterlizations, one or more of the seal areas become compromised and optical performance degrades to an unacceptable level. In contrast, the high cost of traditional reusable endoscopes incorporating, for example, glass optics, militates against disposal of the instrument, even after many more uses. In such cases, the user typically returns the instrument to the manufacturer for expensive refurbishment. The initial cost of the endoscope in accordance with this disclosure is relatively low, and the per-use cost of the endoscope is competitive with or below the per-use cost of traditional reusable scopes, taking into account the initial investment costs, periodic refurbishing costs, and the number of average uses associated with each scope.

While the above description contains many specifics, these specifics should not be construed as limitations on the scope of the disclosure, but merely as an exemplification of preferred embodiments thereof. Those skilled in the art will envision other possible variations that are within the scope and spirit of the disclosure and by the claims appended hereto.

What is claimed is:

1. A method of manufacturing an endoscope, comprising the steps of:

providing a frame of an endoscope, the frame including first and second half sections, the first half section including a groove portion extending along substantially the entire peripheral portion thereof, the second half section including a correspondingly dimensioned and configured tongue portion extending along at least a peripheral portion thereof;

securing the first half section to the second half section by interfitting the tongue portion with the groove portion thereby forming a substantially fluid tight seal at the interface therebetween;

securing an endoscope portion of the endoscope to the frame, the endoscopic portion including at least an objective lens arrangement for forming an image of an object and a relay lens arrangement for transferring the image;

injecting a sealant within an interior of the frame to substantially fill the interior to thereby facilitate liquid tight sealing of the frame whereby fluids are prevented from entering the endoscopic portion; and securing an eyepiece to the frame, the eyepiece including an eyelens arrangement for viewing the image transferred by the relay lens arrangement.

2. The method of claim 1, wherein the step of securing the first half section to the second half section includes applying a cement within the groove portion of the first half section and interfitting the tongue portion of the second half section with the groove portion.

3. The method of claim 1 further including the step of positioning a sleeve member about a proximal end portion of the endoscopic portion.

4. The method of claim 3 further including the step of positioning the sleeve member within a correspondingly dimensioned bore defined within the eyepiece.

5. The method of claim 4 further including the step of applying a sealant at the interface of the sleeve member and the endoscopic portion.

6. The method of claim 5 wherein the sleeve member includes an enlarged distal recessed portion having a longitudinal bore with a cross-sectional dimension greater than a cross-sectional dimension of the proximal end portion of the endoscopic portion to define an annular gap between the sleeve member and the endoscopic portion and wherein the step of applying a sealant includes applying the sealant within the annular gap.

\* \* \* \* \*